United States Patent
Ein-Gal

(10) Patent No.: US 7,310,403 B2
(45) Date of Patent: Dec. 18, 2007

(54) TARGET RECONSTRUCTION

(76) Inventor: Moshe Ein-Gal, 30 Azar Street, Ramat Hasharon, 47203 (IL)

( * ) Notice: Subject to any disclaimer, the term of this patent is extended or adjusted under 35 U.S.C. 154(b) by 138 days.

(21) Appl. No.: 11/378,256

(22) Filed: Mar. 20, 2006

(65) Prior Publication Data

US 2007/0217565 A1   Sep. 20, 2007

(51) Int. Cl.
*A61B 6/03* (2006.01)
(52) U.S. Cl. ............... 378/4; 378/210; 378/901
(58) Field of Classification Search ............ 378/4, 378/210, 901
See application file for complete search history.

(56) References Cited

FOREIGN PATENT DOCUMENTS

GB   2192120 A   * 12/1987

OTHER PUBLICATIONS

Tam, The Construction and Use of Convex Hulls in Limited-Angle Computerized Tomography, 1987, Journal of Nondestructive Evaluation, vol. 6, No. 4, pp. 189-204.*

* cited by examiner

*Primary Examiner*—Edward J. Glick
*Assistant Examiner*—John M Corbett
(74) *Attorney, Agent, or Firm*—Dekel Patent Ltd.; David Klein

(57) ABSTRACT

A method for real-time target reconstruction from target image projections including dividing an object into external and internal sub-objects, acquiring external sub-object data, acquiring internal projections, each internal projection including an internal-internal projection which is the projection of the internal sub-object only as if the external sub-object is null, and an internal-external projection which is the projection of the external sub-object only as if the internal sub-object is null, using the external sub-object data to estimate internal-external projections, subtracting the estimated internal-external projections from the acquired internal projections to obtain internal-internal projections, and reconstructing the internal sub-object from the internal-internal projections.

4 Claims, 2 Drawing Sheets

TARGET RECONSTRUCTION

FIELD OF THE INVENTION

The present invention relates generally to imaging of targets, such as medical targets, and particularly to methods for real-time target reconstruction from target image projections.

BACKGROUND OF THE INVENTION

Computerized tomography (CT) is a well-known method for reconstructing a three-dimensional object distribution from a series of two-dimensional projections obtained from a multiplicity of orientations (views) around the object. Typically, the irradiating beam emanates from a point source, rendering the projections conical. The object is conceptually divided into thin parallel slices individually reconstructed from corresponding slice projections. Projections of an entire slice are required for reconstructing the slice, i.e., the entire slice has to be irradiated.

For example, in many CT scanning systems, an X-ray fan beam is projected along a plane through a patient to a plurality of radiation detectors, which provide measurements of X-ray attenuation through the patient along radial lines defined by the X-ray source and the individual detectors. Measurements are made at a plurality of source positions or views around the patient to obtain sets of measurements representing sets of intersecting radiation beam paths. Reconstructing an image from its projections is implemented by various algorithms. For example, one of the algorithms used for such a reconstruction incorporates spatial filtering of the projections and back projecting the filtered data into the image domain. The image plane (in the two-dimensional case) is divided into small square cells (of width in the order of millimeters) called pixels. The back-projection algorithm associates a detector number with each pixel in the field of view. The back-projection formula also adjusts the detector measurements for each pixel as a function of the distance of the pixel from the source of radiation. These adjustment factors are called weight factors. A back projected image is formed by summing the spatially filtered contribution of detector data for each pixel for all the views. Three-dimensional reconstructions from two-dimensional projections use a methodology similar to that of two-dimensional reconstructions from one-dimensional projections.

Prior art diagnostic CT scanners are stationary devices placed in dedicated rooms. Utilizing CT scanners as a part of a treatment procedure is time consuming and cumbersome. Prior art mobile systems are operable to provide real-time scanning and reconstruction during treatment. Such systems are aimed at reconstructing entire slices and therefore incorporate large x-ray detectors for acquiring entire slices projections.

SUMMARY OF THE INVENTION

The present invention seeks to provide improved methods for real-time target reconstruction from target image projections, as is described more in detail hereinbelow. The invention takes advantage of the fact that diagnostic-quality images of the whole object are often not required. Rather a real-time, lower quality sub-object reconstruction might do. The invention describes a method for producing real-time sub-object reconstruction.

There is provided in accordance with an embodiment of the present invention, a method for real-time target reconstruction from target image projections including dividing an object into external and internal sub-objects, acquiring external sub-object data, acquiring internal projections, each internal projection including an internal-internal projection which is the projection of the internal sub-object only as if the external sub-object is null, and an internal-external projection which is the projection of the external sub-object only as if the internal sub-object is null, using the external sub-object data to estimate internal-external projections, subtracting the estimated internal-external projections from the acquired internal projections to obtain internal-internal projections, and reconstructing the internal sub-object from the internal-internal projections.

Acquiring the external sub-object data may include estimating the external sub-object data. Alternatively, acquiring the external sub-object data may include integrating a previously reconstructed object to obtain target external projections. Still alternatively, acquiring the external sub-object data may include measuring a contour of the object, estimating object density in the external sub-object, and integrating the estimated object density over target external projection line segments to obtain target external projections.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
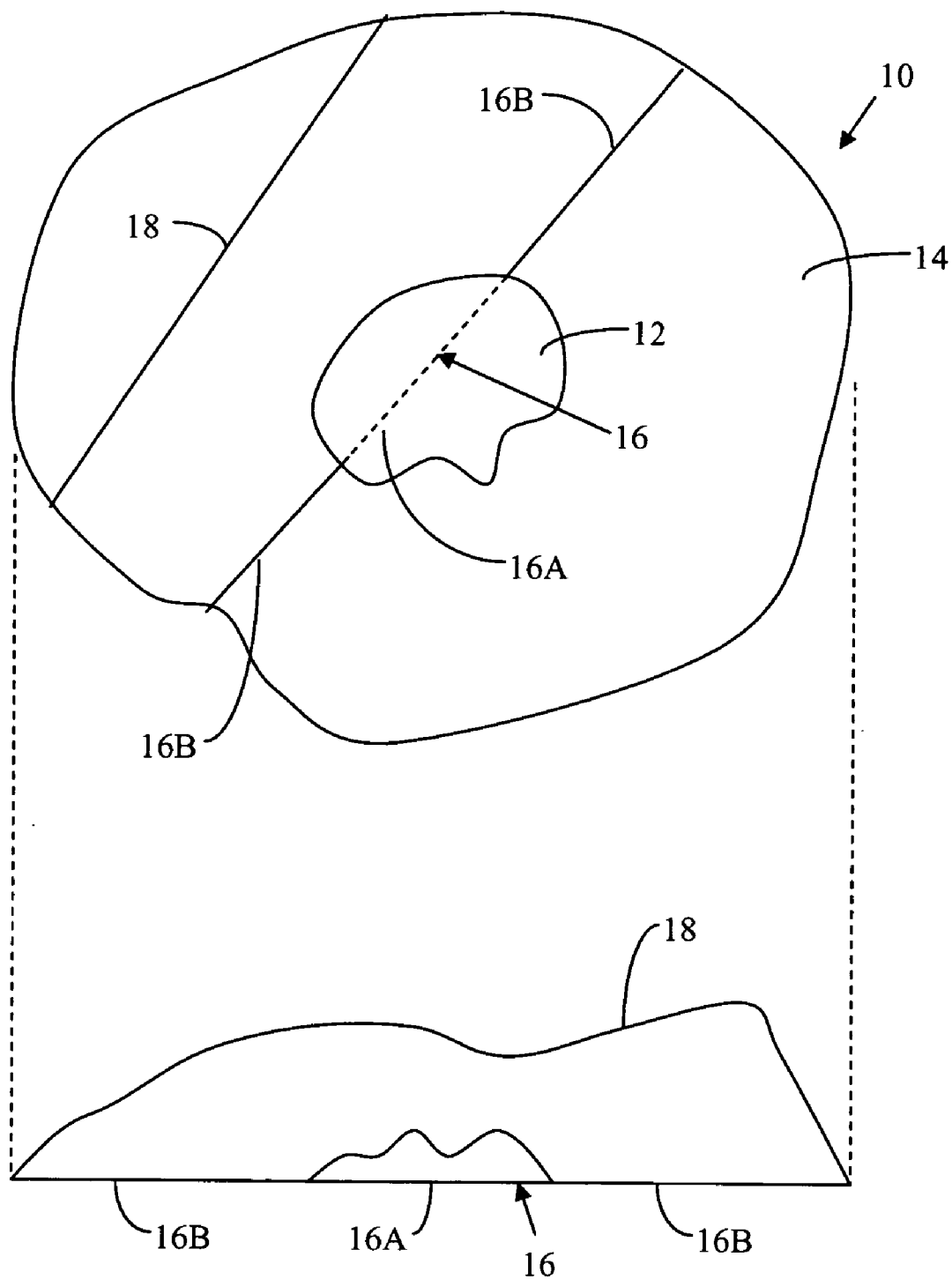
FIG. 1 is a simplified diagram of a division of a target and its surroundings into external and internal sub-images, in accordance with an embodiment of the present invention.

Reference is now made to FIG. 1, which is a diagram of a division of a target and its surroundings into external and internal sub-images, in accordance with an embodiment of the present invention.

An object 10 may contain therein a target 12. The target 12 may be a 3D convex sub-object, although the invention is not limited to convex sub-objects and may be carried out for other shapes as well (e.g., concave). The volume complementary to target 12, i.e., the sub-object outside target 12, is defined as non-target 14. Accordingly, object 10 can be divided into external and internal sub-objects. The internal sub-object is the target 12 (and will alternatively be referred to as internal sub-object or sub-image 12) and the external sub-object is the non-target 14 (and will alternatively be referred to as external sub-object or sub-image 14).

Similarly, projections of object 10 can also be divided into internal and external projections. In other words, internal projections 16 pass through the internal sub-image 12 and external projections 18 pass through the external sub-image 14 only, respectively. Each internal projection 16 can be further divided into two components, namely, an internal-internal projection 16A, which is the projection of the internal sub-object 12 only (as if the external sub-object 14 is null), and an internal-external projection 16B, which is the projection of the external sub-object 14 only, (as if the internal sub-object 12 is null). The invention is based on the observation that the sum of the two components internal-internal projection 16A and internal-external projection 16B equals the internal projection 16.

External sub-object 14 may be reconstructed from external projections 18 only, while internal sub-object reconstruction requires both internal and external projections 16 and 18. This is due to the contributions made by the external sub-object 14 to the internal projections 16, whereas the internal sub-object 12 has no contribution on the external projections 18.

Figure 2:
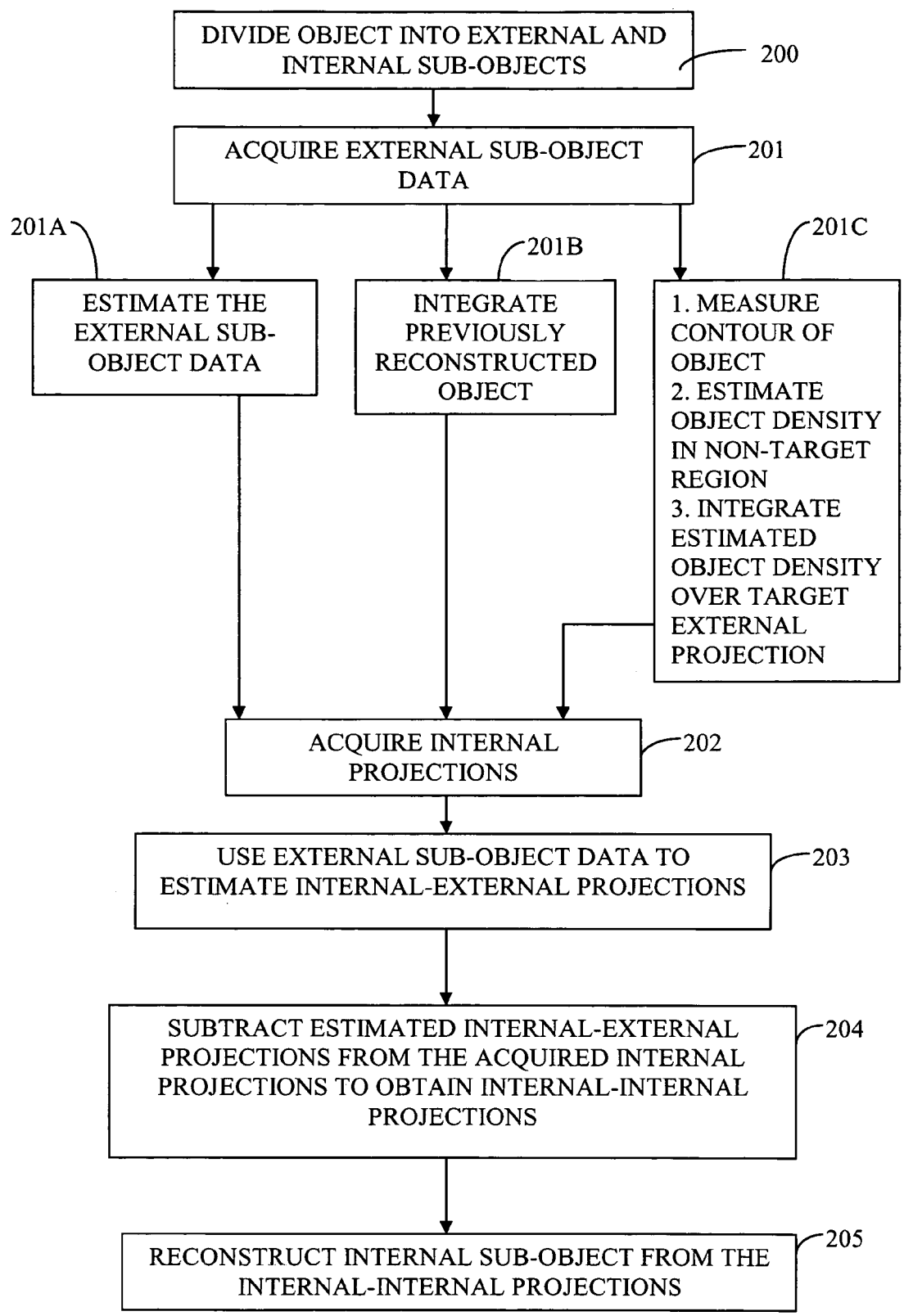
FIG. 2 is a simplified flow chart of a method for real-time target reconstruction from target image projections, in accordance with an embodiment of the present invention.

Reference is now made to FIG. 2, which is a simplified flow chart of a method for reconstructing the internal sub-object by using internal projections and estimating the internal-external projections. In accordance with the method, internal projections may be acquired and internal sub-objects may be reconstructed in real-time during treatment, by using estimated internal-external projections. The estimated internal-external projections can be acquired prior to treatment. A smaller scanner can then be used for the data acquisition in the treatment room.

As shown in FIG. 1, the object 10 can be divided into external and internal sub-objects (step 200). In accordance with a non-limiting embodiment of the present invention, external sub-object data may be acquired (201). The external sub-object data may be obtained in several ways. One way is to simply estimate the external sub-object data (201A). For example, if the target is the prostate gland and the external sub-object is the surrounding tissue, one way of obtaining the external sub-object data would be to estimate the relative sizes of the prostate and surrounding tissue in accordance with known data from a large cross-section of the male human population, e.g., the $95^{th}$ percentile. Another way of estimating the target external projections is by integrating a previously reconstructed object (201B) to obtain the target external projections. For example, a previously obtained ultrasound or CT image of the prostate and surrounding tissue of the particular patient may be used. Still another way of estimating the target external projections is by measuring the contour of the object (e.g., the contour of the tissue surrounding the prostate), estimating the object density in the non-target region (external sub-object), and integrating the estimated object density over the target external projection line segments to obtain the target external projections (201C).

Internal projections may then be acquired by the CT scanner (202). The external sub-object data may be used to estimate internal-external projections (203). The estimated internal-external projections may be subtracted from the acquired internal projections to obtain internal-internal projections (204). The internal sub-object may then be reconstructed from the internal-internal projections (205) by applying known reconstruction algorithms (such as back-projection methods mentioned above).

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. A method for real-time internal sub-object reconstruction from internal sub-object projections comprising:
    dividing an object into external and internal sub-objects;
    acquiring external sub-object data;
    acquiring internal projections, each internal projection comprising an internal-internal projection which is the projection of the internal sub-object only as if the external sub-object is null, and an internal-external projection which is the projection of the external sub-object only as if the internal sub-object is null;
    using the external sub-object data to estimate internal-external projections;
    subtracting estimated internal-external projections from the acquired internal projections to obtain internal-internal projections; and
    reconstructing the internal sub-object from the internal-internal projections.

2. The method according to claim 1, wherein acquiring the external sub-object data comprises estimating the external sub-object data.

3. The method according to claim 1, wherein acquiring the external sub-object data comprises integrating a previously reconstructed object to obtain external sub-object projections.

4. The method according to claim 1, wherein acquiring the external sub-object data comprises:
    measuring a contour of the object;
    estimating object density in the external sub-object; and
    integrating the estimated object density over external sub-object projection line segments to obtain external sub-object projections.

* * * * *